United States Patent
Mohamad Hani et al.

(10) Patent No.: US 8,755,577 B2
(45) Date of Patent: Jun. 17, 2014

(54) METHODOLOGY AND APPARATUS FOR OBJECTIVE, NON-INVASIVE AND IN VIVO ASSESSMENT AND RATING OF PSORIASIS LESION SCALINESS USING DIGITAL IMAGING

(75) Inventors: Ahmad Fadzil Mohamad Hani, Perak (MY); Esa Prakasa, Perak (MY)

(73) Assignee: Institute of Technology Petronas Sdn Bhd, Tronoh Perak (MY)

( * ) Notice: Subject to any disclaimer, the term of this patent is extended or adjusted under 35 U.S.C. 154(b) by 122 days.

(21) Appl. No.: 13/499,784

(22) PCT Filed: May 9, 2011

(86) PCT No.: PCT/MY2011/000043
§ 371 (c)(1),
(2), (4) Date: Apr. 2, 2012

(87) PCT Pub. No.: WO2012/064170
PCT Pub. Date: May 18, 2012

(65) Prior Publication Data
US 2012/0308096 A1    Dec. 6, 2012

(30) Foreign Application Priority Data
Nov. 8, 2010 (MY) ........................... PI 2010005221

(51) Int. Cl.
*G06K 9/00* (2006.01)

(52) U.S. Cl.
USPC .......................................................... 382/128

(58) Field of Classification Search
USPC ........................ 382/128–134; 128/920–925; 356/39–49; 600/407–414, 424–426; 345/581–618; 250/455
See application file for complete search history.

(56) References Cited

U.S. PATENT DOCUMENTS

2007/0060784 A1    3/2007   Ellis
2010/0121201 A1    5/2010   Papaioannou

OTHER PUBLICATIONS

Ahmad Fadzil et al., Thickness Characterization of 3D Skin Surface Images Using Reference Line Construction Approach, Lecture Notes in Computer Science, 2009, vol. 5857/2009, (pp. 448-454).
Hermawan Nugroho et al., "Surface Analysis of Psoriasis for PASI Scaliness Assessment", Intelligent and Advanced Systems, Nov. 2007, (pp. 798-802).
International Search Report for PCT/MY2011/000043, dated Oct. 21, 2011 (6 pages).
Written Opinion for PCT/MY2011/000043, dated Oct. 21, 2011 (5 pages).

*Primary Examiner* — Atiba O Fitzpatrick
(74) *Attorney, Agent, or Firm* — Hamre, Schumann, Mueller & Larson, P.C.

(57) ABSTRACT

The present invention relates generally to a method and apparatus for assessing data from digital images of psoriasis lesion for said psoriasis lesion scaliness by utilizing a developed computer vision system to obtain Psoriasis Area and Severity Index (PASI) parameters in particular.

13 Claims, 7 Drawing Sheets

| Score | PASI Scaliness Description |
|---|---|
| 0 | None |
| 1 | Fine scale |
| 2 | Coarse scale, most lesions partially covered by scales |
| 3 | Coarse scale, almost all lesions covered by a rough surface |
| 4 | Very coarse thick scales covering all lesions, very rough surface |

| Score | PASI Scaliness Description |
|---|---|
| 0 | None |
| 1 | Fine scale |
| 2 | Coarse scale, most lesions partially covered by scales |
| 3 | Coarse scale, almost all lesions covered by a rough surface |
| 4 | Very coarse thick scales covering all lesions, very rough surface |

METHODOLOGY AND APPARATUS FOR OBJECTIVE, NON-INVASIVE AND IN VIVO ASSESSMENT AND RATING OF PSORIASIS LESION SCALINESS USING DIGITAL IMAGING

1. TECHNICAL FIELD OF INVENTION

The present invention relates generally to a method and apparatus for assessing data from digital images of psoriasis lesion for said psoriasis lesion scaliness by utilizing a developed computer vision system to obtain Psoriasis Area and Severity Index (PAST) parameters in particular.

2. BACKGROUND OF THE INVENTION

Psoriasis is common skin disease which is caused by an accelerated replacement of human skin cell. In normal condition, skin cells shed and replace themselves in 21-28 days. But in psoriasis, this process can occur in 2-6 days. Psoriasis can affect any ages, any gender and regardless the race. Around 125 million of people around the worlds are affected, or 2-3% of population is living with psoriasis.

Psoriasis is non-contagious from person to person or between the patient's body part itself. Up to now, there is no solid inference that psoriasis can run in families. Several cases show that children whose parent is psoriasis patient also have psoriasis. But some cases reveal the opposite.

The lesions vary in appearance with the type of psoriasis. About 80% of psoriasis case is plaque psoriasis. This type sometimes is also named psoriasis vulgaris as it means common. Plaque psoriasis lesions have silvery white scales, which are due to skin shedding (effect of accelerated skin growth). The redness of the lesions is due to the increase of blood vessels to support the increase of cell production.

Recent research has found that the change in skin growth is affected by the change in immune system. Certain immune cells (T cell) are triggered and become overactive. T cells act as if they are defending against virus infections or healing skin wounds. This condition accelerates the skin growth causing thick plaque to be formed. Psoriasis usually occurs in knee, elbow, and scalps, but it can also happen in any part of human body. Psoriasis has been shown to have significant impact on quality of life. Due to the appearance of the lesion, individuals with psoriasis are found to have low self-esteem.

There are four known types of treatments for psoriasis. The drug used depends on the severity level. For mild to moderate psoriasis, physicians give topical therapies. It is available in creams, lotions, ointments, mousses, and gels. The topical therapies are applied in localized psoriasis. The second treatment is phototherapy. This therapy uses ultraviolet light A (UVA) and B (UVB), and the phototherapy sessions can last for several weeks. The third treatment is systemic medication which uses tablets or pills. This treatment has potential side effects to the patient, hence only patients with moderate to severe psoriasis undergo this treatment. The fourth or the latest treatment found is biological injection. This treatment only applies t o patients with severe psoriasis which other types of treatment are not effective. The injection will block certain immune cells (T cell) to act, as this accelerated growth is the cause of psoriasis.

Physicians use their knowledge and experience to decide which treatment is to be applied. Patient's physical condition which differs from one another is also a consideration. The treatment therapy can include a combination of treatments with different dosages and depending on the patient's response, the treatment can be changed. Physicians assess the patient's psoriasis severity as well as monitor the treatment efficacy periodically.

The gold standard to assess psoriasis condition is Psoriasis Area and Severity Index (PAST). In PASI, the human body is divided into four body regions: head, trunk, upper extremities and lower extremities. There are four parameters to be determined at the body regions, namely area, erythema (redness), thickness and scaliness of the lesions. Severity is rated for each index on a 0-4 scale (0 for no involvement; 4 for severe involvement) for erythema, thickness and scaliness while 0-6 scale for area. Each body region is weighted according to the proportion of body surface area (BSA). Head is weighted 0.1, trunk is 0.3, upper and lower extremities are 0.2 and 0.4 respectively. PASI score is determined using the following equation:

$$PASI=0.1(R_h+T_h+S_h)A_h+0.2(R_u+T^u+S_u)A_u+0.3(R_t+T_t+S_t)A_t+0.4(R_l+T_l+S_l)A_l$$

A =area (0-6), R=redness or erythema (0-4), T =thickness (0-4), S =scaliness (0-4).

h=head, u=upper extremities, t=trunk, l=lower extremities.

The total PASI score ranges from 0 to 72; higher score indicate more severe psoriasis condition. The treatment is considered effective if the PASI score is reduced by 75% from the initial score.

Although PASI is gold standard to assess the treatment efficacy, this method is tedious and thus rarely used in daily practice. Dermatologist has to assess all lesions and provide scores for each parameter.

Scaliness is one of the parameters of PASI scoring. The scaliness refers to the extent of coarseness of the scale resulting in the roughness of the skin surface. This is due to the amount of stratum corneum that is present on the surface of plaque psoriasis. In order to assess the scaliness of psoriasis lesion, dermatologists observe and feel (usually using the index finger) the lesion condition. For each body region, a representative lesion is chosen for assessment. Dermatologists use their knowledge and experience, and the above assessment procedure to determine the scaliness score. Alternatively, an average scaliness PASI score is determined by selecting the most common lesion in that area. This subjective assessment procedure leads to inter-rater and intra-rater score variations, inaccuracies and inconsistencies. Inter-rater variation is the different scores given by two dermatologists, while intra-rater variation is the different scores given by same dermatologist at different times. Even for one dermatologist, it is possible to have a different score for one lesion if a second assessment is conducted. The high variation in rating a patient from time to time would interfere in determining treatment efficacy. Thus, an objective evaluation of psoriasis lesion scaliness for PASI is needed.

Another method to determine skin surface roughness is by performing biopsy, whereby the said skin samples are cut and analyzed physically. The skin sample is imaged by using scanning electron microscopy to obtain 3D skin surface. This is not recommended because it involves physical removal of the said psoriasis lesion even before knowing the severity of the said lesion. If the severity is low enough that oral or ointment medication can cure said psoriasis lesion, then the initial step of cutting said lesion is really unnecessary.

The 3D-Stylus measurement system has also been used to measure surface roughness of skin. A replica of skin surface is required to represent the original skin surface. The system only measures the replica of skin surface, and it may not measure the original skin directly. Besides, the system needs a trained person to build skin replica for skin roughness measurement.

It is therefore advantageous if the assessment of psoriasis lesion scaliness for PAST is made objective, non-invasive and assessed in vivo. This is important in deciding the treatment efficacy, especially in clinical trials. It is yet another advantageous if the assessment could be used in daily practice and performed by regular physicians.

The present invention overcomes the above shortcomings by providing a method and apparatus for assessing data from digital images of psoriasis lesion for said psoriasis lesion scaliness by utilizing a developed computer vision system to obtain Psoriasis Area and Severity Index (PASI) parameters in particular.

3. SUMMARY OF THE INVENTION

Accordingly, it is the primary aim of the present invention to provide a method and apparatus for objective, non-invasive and in vivo assessment for PASI scoring of psoriasis lesion scaliness based on digital image.

It is yet another objective of the present invention to provide a method and apparatus for objective, non-invasive and in vivo assessment and rating of psoriasis lesion scaliness wherein the assessment of scaliness can be done objectively and consistently without being influenced by other characteristic of the lesion such as area, pattern and boundary.

It is yet another objective of the present invention to provide a method and apparatus for objective, non-invasive and in vivo assessment and rating of psoriasis lesion scaliness that has the potential to minimize variations of PASI score due to inter-rater and intra-rater, thus making it more accurate.

It is yet another objective of the present invention to provide a method and apparatus for objective, non-invasive and in vivo assessment and rating of psoriasis lesion scaliness that can be applied on any skin colour.

Other and further objects of the invention will become apparent with an understanding of the following detailed description of the invention or upon employment of the invention in practice.

According to a preferred embodiment of the present invention there is provided,

A method for objective, non-invasive and in vivo assessment and rating of psoriasis lesion scaliness using digital imaging comprising:
  i. acquiring 3D digital image of patient (301);
  ii. averaging the subtraction result to determine PASI scaliness value (307);
characterised in that said method for objective, non-invasive and in vivo assessment and rating of psoriasis lesion scaliness using digital imaging is done by the sub-steps of:
  a. acquiring 3D and 2D images of assessed surfaces (301);
  b. segmenting psoriasis lesion area from the normal skin area (302);
  c. mapping the pixel coordinates of the segmented lesion in 2D image to the lesion area in 3D image (303);
  d. partitioning said segmented lesion area into sub-divided lesion area (304);
  e. constructing an estimated surface of the lesion using polynomial surface fitting (305);
  f. determining the goodness of polynomial fitting of the subdivided lesion area;
  g. subtracting the respective estimated surface from the actual lesion surface (306);
  h. averaging the absolute value of subtraction result to determine surface roughness of each sub-divided lesion surfaces (307);
  i. averaging the surface roughness of each sub-divided lesion surfaces to obtain overall surface roughness (308);
  j. correlating the overall surface roughness of lesion surface with PASI scaliness score (309).

In a second embodiment of the present invention, there is provided,

A method for objective, non-invasive and in vivo assessment and rating of psoriasis lesion scaliness using digital imaging comprising:
  i. acquiring 3D digital image of patient (501);
  ii. averaging the subtraction result to determine PASI scaliness value (307);
characterised in that said method for objective, non-invasive and in vivo assessment and rating of psoriasis lesion scaliness using digital imaging is done by the sub-steps of:
  a. acquiring 3D image of assessed surfaces (501);
  b. segmenting and cropping psoriasis lesion area from the normal skin area (502);
  c. converting said segmented lesion into a file containing surface information in (X, Y, Z) coordinates (503);
  d. partitioning said segmented lesion area into sub-divided lesion area (304);
  e. constructing an estimated surface of the lesion using polynomial surface fitting (305);
  f. determining the goodness of polynomial fitting of the subdivided lesion area;
  g. subtracting the respective estimated surface from the actual lesion surface (306);
  h. averaging the absolute value of subtraction result to determine surface roughness of each sub-divided lesion surfaces (307);
  i. averaging the surface roughness of each sub-divided lesion surfaces to obtain overall surface roughness (308);
  j. correlating the overall surface roughness of lesion surface with PASI scaliness score (309).

In another embodiment of the present invention, there is provided,

An apparatus for objective, non-invasive and in vivo assessment and rating of psoriasis lesion scaliness using digital imaging comprising:
  i. at least one 3D scanner, together with at least one scanner lead;
  ii. at least one electrical signal connecting means;
characterized in that
further comprises at least one any acceptable electronic processing means to acquire and average out the subtraction result to determine the PASI scaliness score.

4. BRIEF DESCRIPTION OF THE DRAWINGS

Other aspects of the present invention and their advantages will be discerned after studying the Detailed Description in conjunction with the accompanying drawings in which.

5. DETAILED DESCRIPTION OF THE DRAWINGS

In the following detailed description, numerous specific details are set forth in order to provide a thorough understanding of the invention. However, it will be understood by those or ordinary skill in the art that the invention may be practised without these specific details. In other instances, well known methods, procedures and/or components have not been described in detail so as not to obscure the invention.

The invention will be more clearly understood from the following description of the methods thereof, given by way of example only with reference to the accompanying drawings. In the descriptions that follow, like numerals represent like elements in all figures. For example, where the numeral (2) is used to refer to a particular element in one figure, the numeral (2) appearing in any other figure refers to the same element.

Figures 1, 2A:
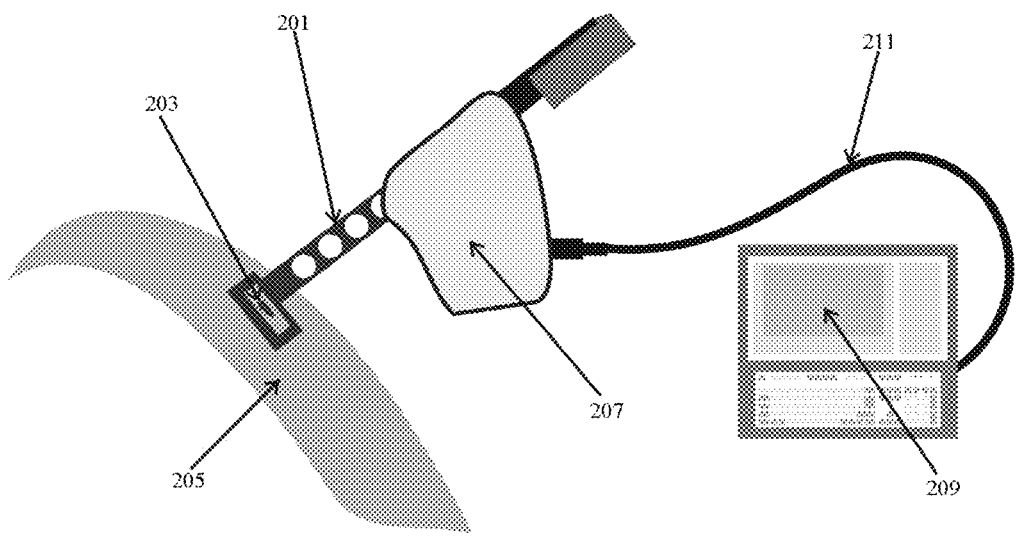
FIG. 1 is a table showing the description of each PAST lesion scaliness score.
FIG. 2A shows the scheme of a 3D optical scanner connected to the software to obtain 2D and 3D image of psoriasis lesion.

Referring now to FIG. 1, there is a table showing the description of each PASI lesion scaliness score. It is graded by score 0 to 4 with 0 for none scale on skin and 4 for very coarse thick scales covering all lesions and very rough surface. The other two parameters are graded by score 1 to 3 with higher score indicating more severe condition.

Referring now to FIG. 2A, there is shown a scheme of a 3D optical scanner (207) connected to an electronic processing means (209), which may be a software to obtain 2D and 3D image of psoriasis lesion. A non-contact 3D optical scanner, together with a scanner lead (201) is used to capture the images. The setting for optical scanner (207) should be approximately 64 μm lateral resolution and 4 μm depth resolution. The setting must be set in order to achieve the elevation accuracy of a minimum 0.04 mm to perform the said algorithm. The said 3D optical scanner (207) is connected to electronic processing means (209) by electrical signal connecting means (211). With the aid of software, the said algorithm has been developed by using polynomial surface fitting to generate the said surface roughness lesion surface and hence to determine the PASI scaliness value. Images are taken with a fixed distance between patient skin (205) and 3D optical scanner (207) and a fixed picture size to avoid re-calibration of the system.

Figure 2B:
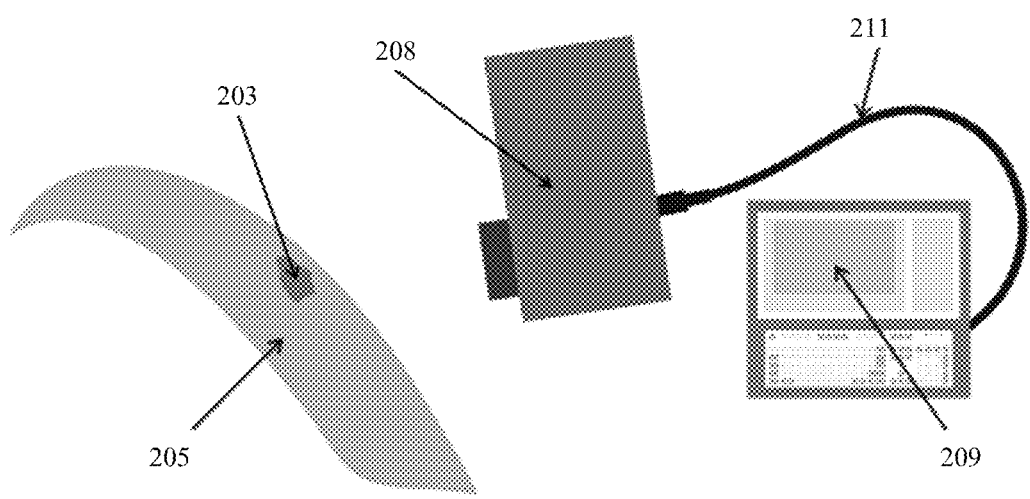
FIG. 2B shows the scheme of 3D laser scanner connected to the software to obtain 3D image of psoriasis lesion.

Referring now to FIG. 2B, there is depicted a scheme of a 3D laser scanner (208) connected to an electronic processing means (209), which may be a software to obtain 3D image of psoriasis lesion (203) on skin surface (205). The said 3D laser scanner (208) is connected to electronic processing means (209) by electrical signal connecting means (211).

Figure 3:
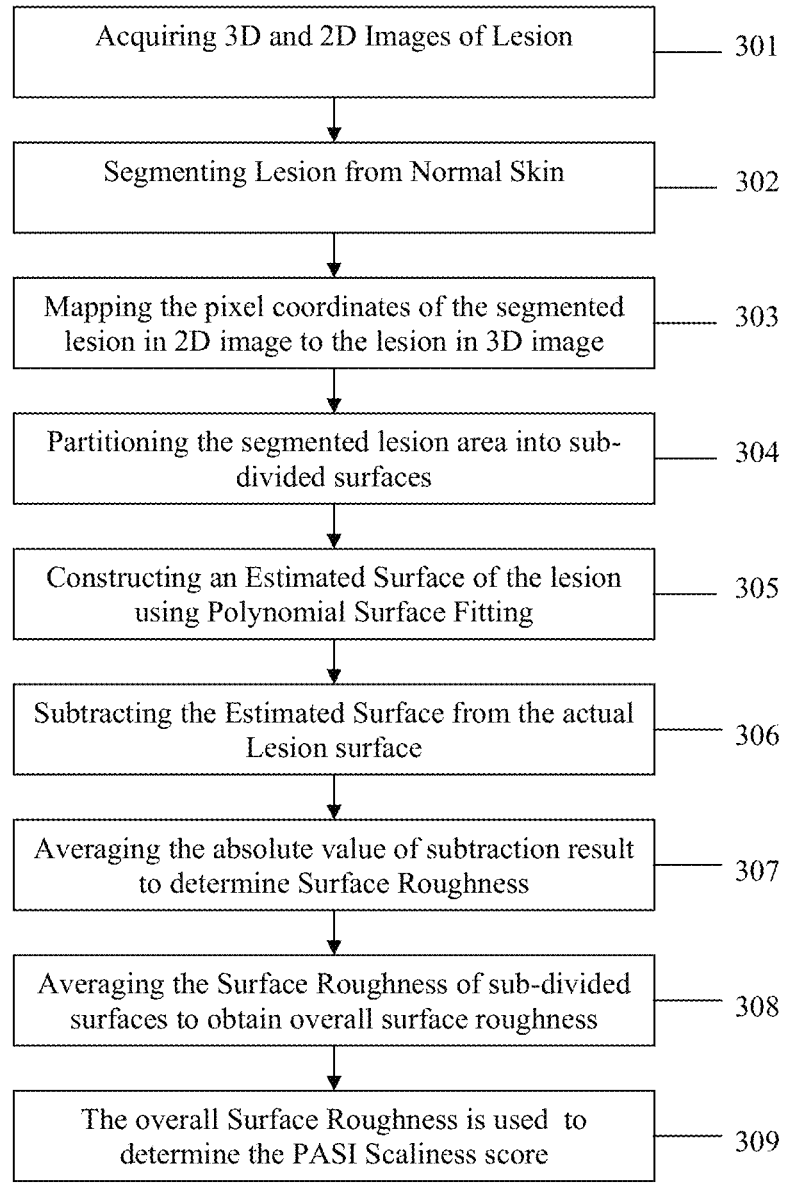
FIG. 3 is a flow chart showing a block diagram outlining the general steps of psoriasis lesion scaliness assessment using 3D optical scanner device.

Referring now to FIG. 3, there is shown a flow chart outlining the general steps of psoriasis lesion scaliness assessment to determine the score for PASI scaliness. The assessment comprises the first psoriasis lesion scaliness assessment step indicated by the first block (301), the second psoriasis lesion scaliness assessment step indicated by the second block (302), the third psoriasis lesion scaliness assessment step indicated by the third block (303), the fourth psoriasis lesion scaliness assessment step indicated by the fourth block (304), the fifth psoriasis lesion scaliness assessment step indicated by the fifth block (305), the sixth psoriasis lesion scaliness assessment step indicated by the sixth block (306), the seventh psoriasis lesion scaliness assessment step indicated by the seventh block (307), the eighth psoriasis lesion scaliness assessment step indicated by the eighth block (308), and the last psoriasis lesion thickness assessment step indicated by the ninth block (309).

Figure 4A:
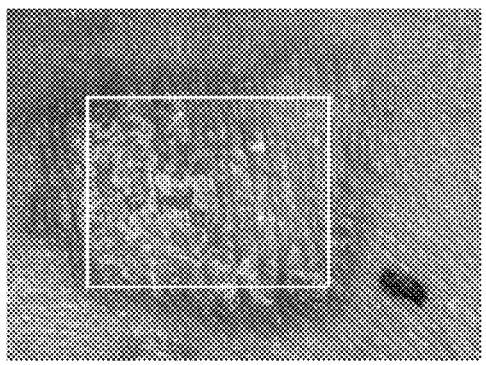
FIG. 4A to 4F shows the graphical images outlining the general steps of psoriasis lesion scaliness assessment.
Figure 4B:
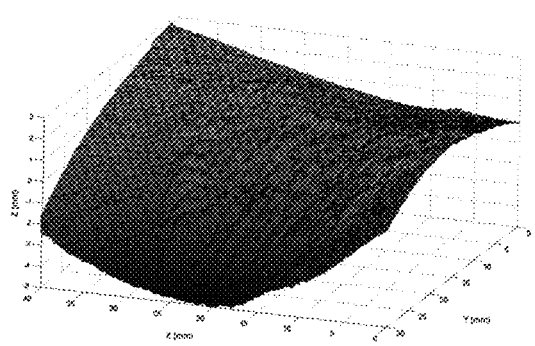

From the said flow chart, it can be seen that the first step is acquiring 2D and 3D digital images as shown in FIGS. 4A and 4B respectively, as indicated by the first block of FIG. 3 (301) using a 3D optical scanner device. During the process of acquiring image, the distance between patient skin and 3D optical scanner is fixed according to the setting requirement of the said optical scanner.

The second step is segmenting the lesion from normal skin as described by the second block of FIG. 3 (302). The shape of segmentation area is a rectangle as shown in FIG. 4A. The segmented area shall only covers the lesion surface, and the coverage area is always less than the total area of lesion.

Figure 4C:
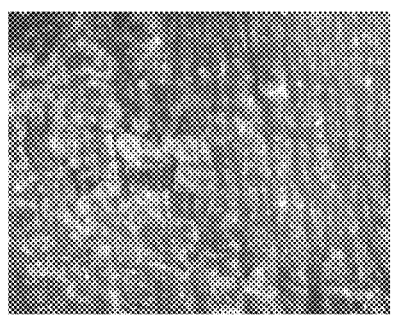
Figure 4D:
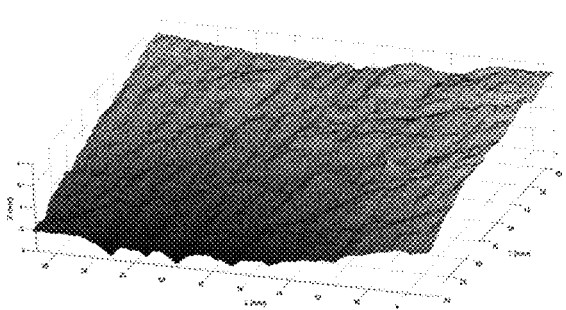

Once the lesion has been segmented from the normal skin, the next step is mapping the pixel coordinates of the segmented lesion in 2D image to the lesion area in 3D image, as indicated by the third block of FIG. 3 (303). Coordinate points of lesion segmented area are used as the reference for extracting the lesion segmented area of 3D surface. The lesion segmented area in 2D and 3D image are shown in FIG. 4C and 4D respectively.

Figure 4E:
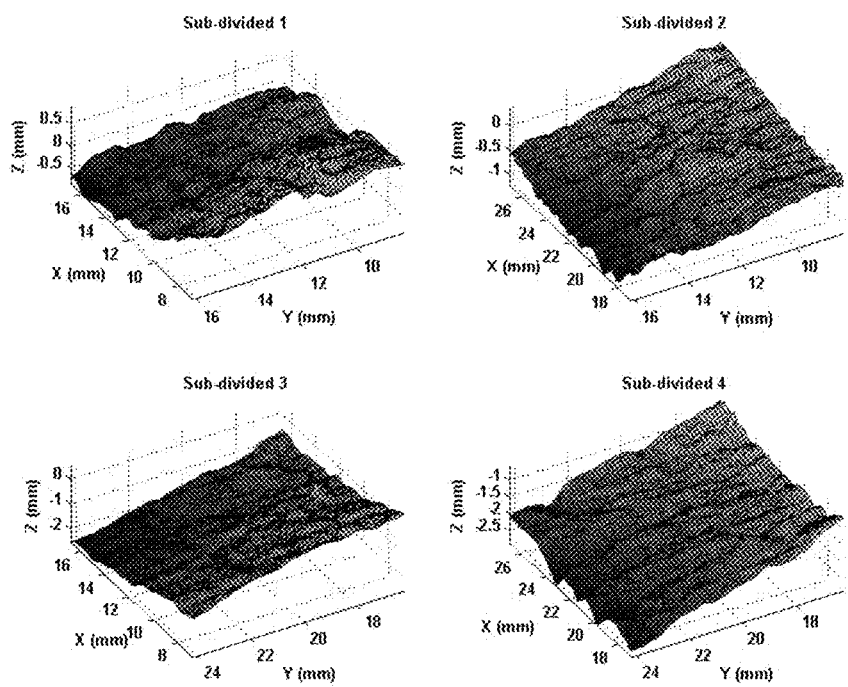

The fourth step is partitioning the segmented lesion area into smaller sub-divided surfaces, as described by fourth block of FIG. 3 (304). Polynomial surface fitting can be improved by applying to the smaller surfaces. The number of sub-divided surfaces is 2×2 surfaces. FIG. 4E displays four sub-divided surfaces of sub-divided 1, 2, 3, and 4.

The estimated surface is then constructed using polynomial surface fitting. This step is indicated by the fifth block of FIG. 3 (305). Polynomial surface fitting is used as surface fitting method since it is simple to apply. Polynomial is a best-fitting method that enables the estimated surface to follow the curvature of lesion surface. Polynomial surface fitting is applied to each sub-divided of lesion surface separately. In the algorithm, second and third order polynomials are used. The equations for second and third order polynomial are shown in (1) and (2) respectively.

$$Z_2(x,y)=(a_1x^2+a_2x+a_3)y^2+(a_4x^2+a_5x+a_6)y+(a_7x^2+a_8x+a_9) \quad (1)$$

$$Z_3(x,y)=(a_1x^3+a_2x^2+a_3x+a_4)y^3+(a_5x^3+a_6x^2+a_7x+a_8)y^2+(a_9x^3+a_{10}x^2+a_{11}x+a_{12})y+(a_{13}x^3+a_{14}x^2+a_{15}x+a_{16}) \quad (2)$$

Z as a function of f (x, y) is the elevation value, while a is the polynomial coefficient and X, y is the respective coordinate. Second order polynomial of surface fitting and third order polynomial has 9 and 16 polynomial coefficients, respectively.

There are two steps to perform polynomial surface fitting. First is to find a matrix of polynomial coefficient using matrix equation as shown in (3) using every coordinate [X, Y] and elevation value [Z] of lesion surface.

$$[a]=[X,Y]^{-1}[Z] \quad (3)$$

After obtaining the polynomial coefficients matrix [a], the estimated surface $[Z_{est}]$ in every coordinates [X,Y] can be determined using (4).

$$[Z_{est}]=[a][X,Y] \quad (4)$$

The goodness of polynomial fitting can be assessed by using the equation of coefficient of determination ($R^2$). Surface fitting result is considered fit the surface properly if its $R^2$ value within 0.9 to 1. The equation for coefficient of determination ($R^2$) can be written as $$R^2 = \frac{\sum_{i=1}^{N}(x_i - \bar{x})(y_i - \bar{y})}{\sqrt{(x_i - \bar{x})^2}\sqrt{(y_i - \bar{y})^2}} \quad (5)$$

Once the estimated surface is constructed, the estimated surface is subtracted from the actual lesion surface to obtain the elevation surface. This step is indicated by the sixth block of FIG. 3 (306). The equation as shown in (6) describes the subtraction of lesion surface [Z] and the estimated surface [$Z_{est}$].

$$[h_{i,j}]=[Z]-[Z_{est}] \quad (6)$$

The absolute value of subtraction result is then averaged to determine the surface roughness ($R_a$) of elevation surfaces, as described by the seventh block of FIG. 3 (307). $R_a$ is selected as roughness index at roughness algorithm. The $R_a$ equation is applied to whole elevation surface. The equation for elevation surface with size M×N can be written as per equation (7).

$$R_a = \frac{1}{MN}\sum_{i=1}^{M}\sum_{j=1}^{N}|h_{i,j}| \quad (7)$$

The eighth step is averaging the surface roughness of subdivided surfaces determining surface roughness ($R_a$) of elevation surfaces. This step is indicated by the eighth block of FIG. 3 (308).

$$R_a = \sum_{i=1}^{4}\frac{R_{a,i}}{4} \quad (8)$$

For the example, $R_a$ of each sub-divide surface are $R_{a,1}$ ($1^{st}$ sub-divided surface)=0.080 mm, $R_{a,2}$ ($2^{nd}$ sub-divided surface)=0.067 mm, $R_{a,3}$ ($3^{rd}$ sub-divided surface)=0.073 mm and $R_{a,4}$ (4th sub-divided surface)=0.083 mm. Hence, the surface roughness ($R_a$) of elevation surfaces is:

$$R_a = \frac{0.080 + 0.067 + 0.073 + 0.083}{4} = 0.0758 \cong 0.076 \text{ mm}$$

The last stage is correlating the overall surface roughness with PASI Scaliness score, as indicated by the ninth block of FIG. 3 (309). The classification of PASI Scaliness scores are as follows:
Score 1: $R_a \leq 0.028$ mm
Score 2: $0.028 < R_a \leq 0.042$ mm
Score 3: $0.042 < R_a \leq 0.062$ mm
Score 4: $R_a > 0.062$ mm Psoriasis lesions is classified into 4 score groups by applying k-Means clustering as an unsupervised clustering algorithm. Psoriasis lesions are obtained from 104 psoriasis patients (84 males, 20 females) of Department of Dermatology, Hospital Kuala Lumpur. Total number of psoriasis lesion is 721 lesions. The objective of the k-Means algorithm is to divide the dataset into k clusters. The basic form of the k-Means algorithm is based on alternating two stages. The first stage is assignment of data points into cluster groups. A data point is assigned to the group which is nearest in the Euclidean distance to the group centroid. The second stage is the calculation of new group centroids based on the new assignments. The stages will be terminated when the group centroids are maximally separated and no new assignment required.

Roughness centroid of each PASI Scaliness score is determined by applying K-mean clustering algorithm. Dataset is divided into 4 groups to represent four scores of PASI Scaliness. Boundary level between two adjacent score groups is determined by finding the middle point between means of adjacent groups. Table 1 lists means and boundary levels of PASI scaliness scores.

TABLE 1

Centroids and Boundary Levels of PASI Scaliness Scores (N = 721)

| PASI Score | Score Centroid (mm) | N | Boundary level (mm) |
|---|---|---|---|
| 1 | 0.021 | 212 | $R_a \leq 0.028$ |
| 2 | 0.034 | 275 | $0.028 < R_a \leq 0.042$ |
| 3 | 0.050 | 171 | $0.042 < R_a \leq 0.062$ |
| 4 | 0.074 | 63 | $0.062 < R_a$ |

K-Means clustering algorithm's ability to classify psoriasis lesion based on surface roughness is validated. Validation is conducted by applying clustering algorithm to the divided dataset. Dataset is randomly partitioned into two equal sized datasets (Dataset 1 and Dataset 2). The consistency of score means for all dataset shows that the scores are properly clustered (maximally separated). Score means are not influenced by dataset partition since the size of dataset is still large. K-Means clustering algorithm requires a large dataset for each score to achieve centroid stability. Table 2 describes stability of score means of partitioned datasets. The mean differences of each score between Dataset 1 and Dataset 2 are not greater than 0.002 mm.

TABLE 2

Centroids and Boundary Levels of PASI Scaliness Scores of Dataset 1 and Dataset 2

| | Dataset 1 (N = 360) | | Dataset 2 (N = 361) | | |
|---|---|---|---|---|---|
| PASI Score | Score Centroid (mm) | N | Score Centroid (mm) | N | Centroid difference (mm) |
| 1 | 0.021 | 99 | 0.022 | 116 | 0.001 |
| 2 | 0.033 | 138 | 0.035 | 130 | 0.002 |
| 3 | 0.049 | 95 | 0.050 | 80 | 0.001 |
| 4 | 0.074 | 28 | 0.073 | 35 | 0.001 |

The boundary levels in Table 1 are then used to classify PASI Scaliness score. In this case, $R_a$ equals to 0.076 mm can be classified as score 4, since a lesion will be scored with score 4 if $R_a > 0.062$ mm.

Referring now to FIG. 4A-4F, there is shown the graphical images outlining the general steps of psoriasis lesion scaliness assessment. Lesion roughness is determined by applying surface roughness algorithm. The 2D image is used to identify boundary of lesion area. The lesion area is segmented from the scanned image as a rectangular image of 3D surface. The surface roughness algorithm is applied to the 3D surface of lesion area. FIGS. 4A and 4B show the scanned image in both 2D and 3D surfaces. The segmented area is indicated by white box on FIG. 4A. The segmented area must not include the normal skin area. FIG. 4C and 4D display the segmented surface in both 2D and 3D images.

The lesion surface is divided into 2×2 sub surfaces to avoid over-fitting of the polynomial surface fitting. FIG. 4E describes the segmented and the sub divided surfaces of lesion surface. The $1^{st}$, $2^{nd}$, $3^{rd}$, and $4^{th}$ sub divided surfaces are located at top left, top right, bottom left, and bottom right of divided surface respectively.

Figure 4F:
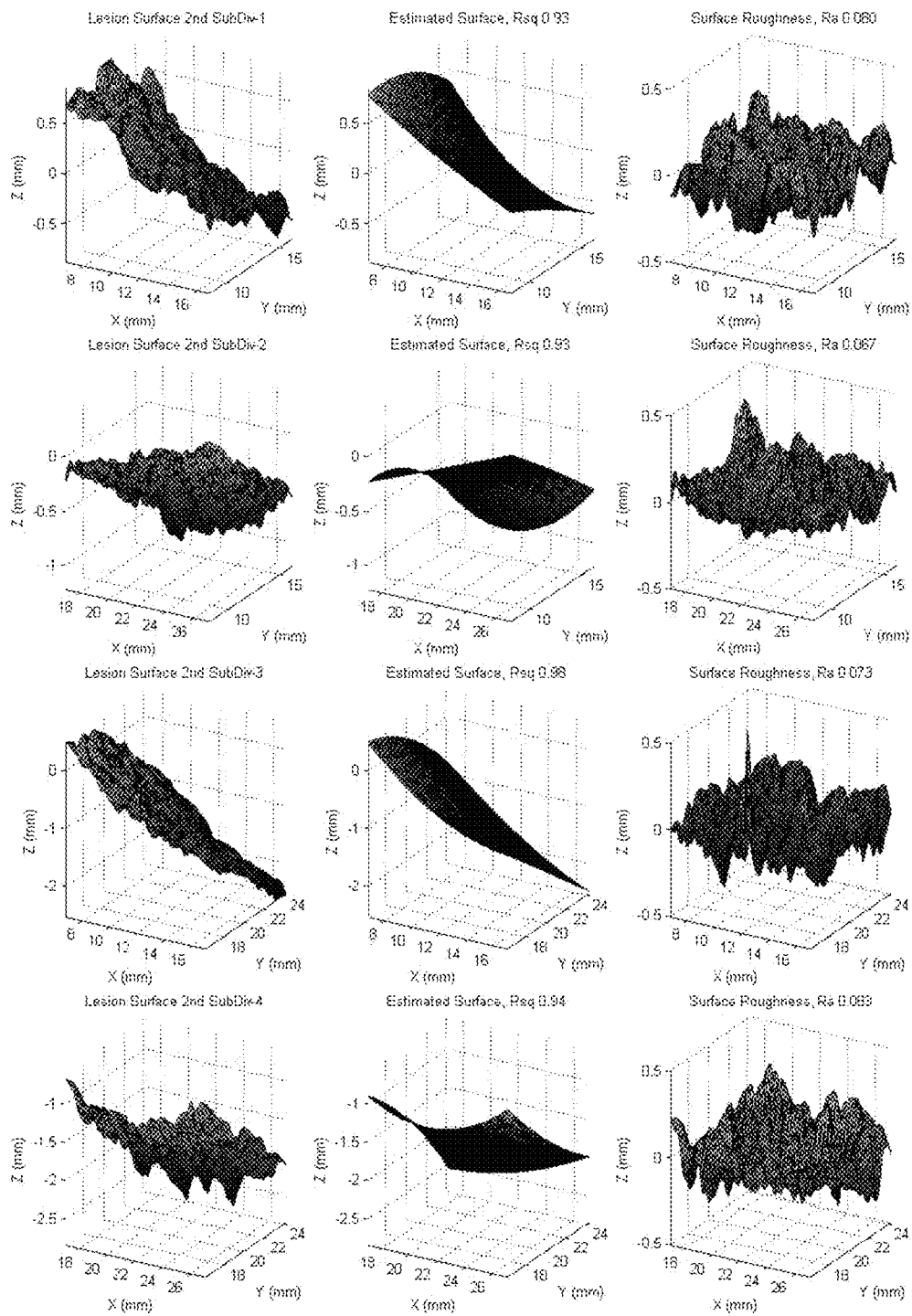

Referring now to FIG. 4F shows the lesion surface, estimated surface, and elevation surface of four sub divided surfaces of FIG. 4E (1)-(4). The estimated surfaces are generated by applying polynomial surface fitting. To calculate the total surface roughness, surface roughness of sub-divided surfaces is averaged. The surface roughness of sub-divided surface can be excluded from calculation, if $R^2$ value of sub-divided surface is less than 0.9.

Figure 5:
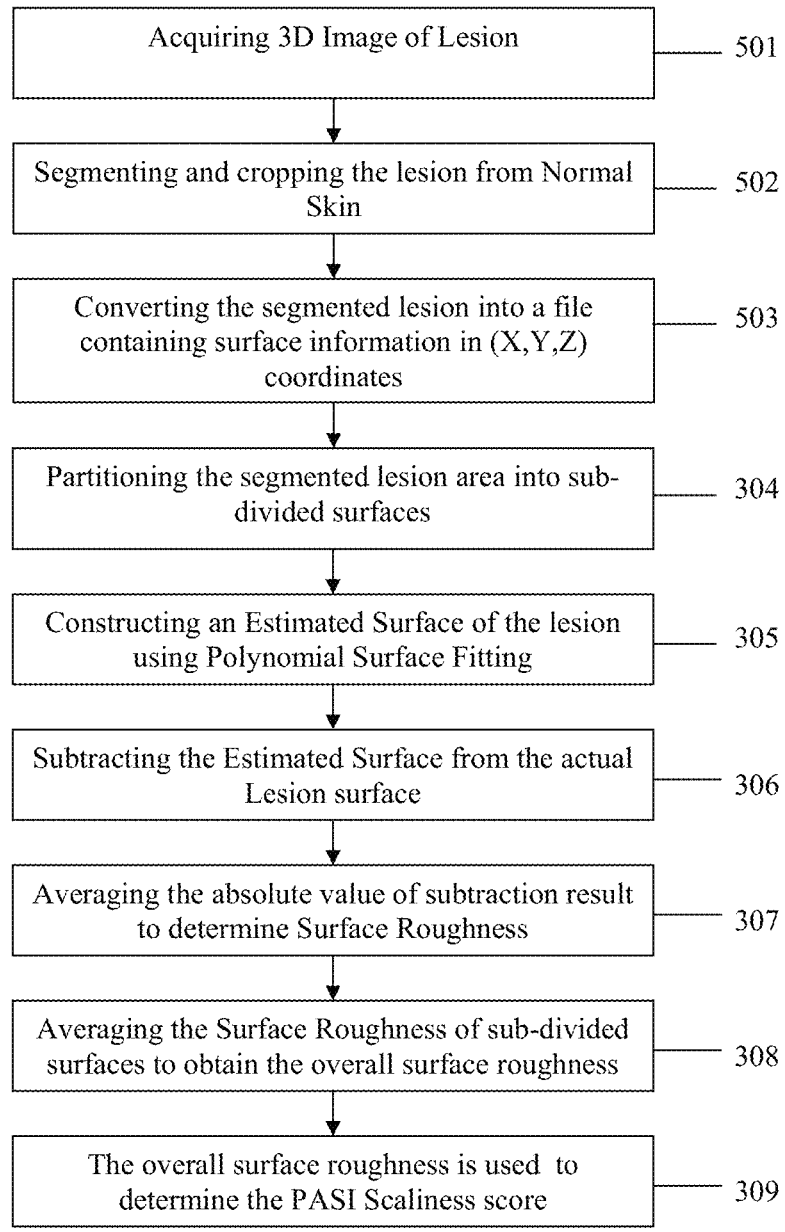
FIG. 5 is a flow chart showing a block diagram outlining the general steps of psoriasis lesion scaliness assessment using 3D laser scanner device.

Referring now to FIG. 5, there is shown a flow chart outlining the general steps of psoriasis lesion scaliness assessment using 3D laser scanner device. Comparing to flow chart on FIG. 3, it can be seen that the steps involved for psoriasis lesion scaliness assessment are almost similar, except for the first block (501), second block (502) and third block (503).

When 3D laser scanner device is being used, the first step is started by acquiring 3D digital image of lesion as indicated by the first block of FIG. 5 (501). A 3D laser scanner device includes a 3D laser camera. During the process of acquiring image, the distance between patient skin and 3D laser scanner is set according to the type of lens used in the said laser scanner.

The second step is segmenting the lesion from normal skin as described by the second block of FIG. 5 (502). The shape of segmentation area is a rectangle as shown in FIG. 4A. The segmented area shall only cover the lesion surface, and the coverage area is always less than the total area of lesion.

Once the lesion has been segmented from the normal skin, the next step is converting the segmented lesion into a file containing surface information in (X,Y,Z) coordinates, as indicated by the third block of FIG. 5 (503). The lesion segmented area in 3D image are shown in FIG. 4D. The process of psoriasis lesion assessment is same as illustrated in FIG. 3 from fourth step (504) and onwards.

While the preferred embodiment of the present invention and its advantages has been disclosed in the above Detailed Description, the invention is not limited there to but only by the spirit and scope of the appended claim.

What is claimed is:

1. A method for objective, non-invasive and in vivo assessment and rating of psoriasis lesion scaliness using digital imaging comprising:
   i. acquiring a 3D digital image of a patient;
   ii. averaging a subtraction result to determine a Psoriasis Area and Severity Index (PASI) scaliness value, wherein the subtraction result is determined by subtracting an estimated surface from an actual lesion surface;
   wherein said method for objective, non-invasive and in vivo assessment and rating of psoriasis lesion scaliness using digital imaging comprises sub-steps of:
      a. acquiring 3D and 2D images of assessed surfaces;
      b. segmenting a psoriasis lesion area from a normal skin area;
      c. mapping pixel coordinates of a segmented psoriasis lesion area in 2D image to a segmented psoriasis lesion area in 3D image;
      d. partitioning said segmented psoriasis lesion area into at least one sub-divided lesion area;
      e. constructing the estimated surface of the sub-divided lesion area using a polynomial surface fitting;
      f. determining a goodness of the polynomial surface fitting of the sub-divided lesion area;
      g. subtracting the respective estimated surface from the actual lesion surface;
      h. averaging an absolute value of the subtraction result to determine a surface roughness of each of the at least one sub-divided lesion area;
      i. averaging the surface roughness of each of the at least one sub-divided lesion area to obtain an overall surface roughness;
      j. correlating the overall surface roughness with a PASI scaliness score.

2. A method for objective, non-invasive and in vivo assessment and rating of psoriasis lesion scaliness using digital imaging as claimed in claim 1, wherein said 3D and 2D images are acquired by a 3D digital image capturing apparatus including a 3D optical scanner.

3. A method for objective, non-invasive and in vivo assessment and rating of psoriasis lesion scaliness using digital imaging comprising:
   i. acquiring a 3D digital image of a patient;
   ii. averaging a subtraction result to determine a Psoriasis Area and Severity Index (PASI) scaliness value, wherein the subtraction result is determined by subtracting an estimated surface from an actual lesion surface;
   wherein said method for objective, non-invasive and in vivo assessment and rating of psoriasis lesion scaliness using digital imaging comprises sub-steps of:
      a. acquiring 3D images of assessed surfaces;
      b. segmenting and cropping a psoriasis lesion area from a normal skin area;
      c. converting a segmented psoriasis lesion area into a file containing a surface information in (X, Y, Z) coordinates;
      d. partitioning said segmented psoriasis lesion area into at least one sub-divided lesion area;
      e. constructing the estimated surface of the sub-divided lesion area using a polynomial surface fitting;
      f. determining a goodness of the polynomial surface fitting of the sub-divided lesion area;
      g. subtracting the respective estimated surface from the actual lesion surface;
      h. averaging an absolute value of the subtraction result to determine a surface roughness of each of the at least one sub-divided lesion area;
      i. averaging the surface roughness of each of the at least one sub-divided lesion area to obtain an overall surface roughness;
      j. correlating the overall surface roughness with a PASI scaliness score.

4. A method for objective, non-invasive and in vivo assessment and rating of psoriasis lesion scaliness using digital imaging as claimed in claim 3, wherein said 3D digital image is acquired by a 3D digital image capturing apparatus including a 3D laser scanner.

5. A method for objective, non-invasive and in vivo assessment and rating of psoriasis lesion scaliness using digital imaging as claimed in claim 1, wherein said step of segmenting the psoriasis lesion area from the normal skin area is performed manually.

6. A method for objective, non-invasive and in vivo assessment and rating of psoriasis lesion scaliness using digital imaging as claimed in claim 1, wherein said step of segmenting the psoriasis lesion area from the normal skin area is performed by identifying and selecting a scanned surface of the psoriasis lesion area.

7. A method for objective, non-invasive and in vivo assessment and rating of psoriasis lesion scaliness using digital imaging as claimed in claim 1, wherein said polynomial surface fitting is achieved by performing the following sub-steps:
   i. finding a polynomial coefficient matrix by using a coordinate and an elevation value of a lesion surface;
   ii. determining the estimated surface in the coordinate;
   iii. evaluating the goodness of the polynomial fitting by using an equation of coefficient of determination.

8. A method for objective, non-invasive and in vivo assessment and rating of psoriasis lesion scaliness using digital imaging as claimed in claim 7, wherein a surface fitting result is considered to fit the respective estimated surface if a coefficient of determination value is within 0.9 to 1.

9. A method for objective, non-invasive and in vivo assessment and rating of psoriasis lesion scaliness using digital imaging as claimed in claim 1, wherein when said surface roughness has a low goodness of fitting, said surface roughness is excluded from the averaging of the surface roughness.

10. A method for objective, non-invasive and in vivo assessment and rating of psoriasis lesion scaliness using digital imaging as claimed in claim 1, wherein said step of correlating the overall surface roughness with the PASI scaliness score is performed by using the following classification:
   i. Score 1 referring to $R_a \leq 0.028$ mm;
   ii. Score 2 referring to $0.028$ mm$<R_a \leq 0.042$ mm;
   iii. Score 3 referring to $0.042$ mm$<R_a \leq 0.062$ mm;
   iv. Score 4 referring to $R_a > 0.062$ mm.

11. An apparatus for objective, non-invasive and in vivo assessment and rating of psoriasis lesion scaliness using digital imaging comprising:
   i. at least one 3D scanner, together with at least one scanner lead;
   ii. at least one electrical signal connecting means;
   wherein the apparatus further comprises at least one electronic processing means to capture and average out a subtraction result to determine a Psoriasis Area and Severity Index (PASI) scaliness value, wherein the subtraction result is determined by subtracting an estimated surface from an actual lesion surface.

12. An apparatus for objective, non-invasive and in vivo assessment and rating of psoriasis lesion scaliness using digital imaging as claimed in claim 11, wherein said 3D scanner is a 3D optical scanner.

13. An apparatus for objective, non-invasive and in vivo assessment and rating of psoriasis lesion scaliness using digital imaging as claimed in claim 11, wherein said 3D scanner is a 3D laser scanner.

* * * * *